United States Patent

Bryant

[11] Patent Number: 5,676,160
[45] Date of Patent: Oct. 14, 1997

[54] SURGICAL METHOD

[76] Inventor: Benjamin Jay Bryant, 7639 St. Marys Lake Rd., Battle Creek, Mich. 49017

[21] Appl. No.: 381,509

[22] Filed: Jan. 31, 1995

[51] Int. Cl.$^6$ ................................................ A61B 17/00
[52] U.S. Cl. ........................................................ 128/898
[58] Field of Search ............................................ 128/898

[56] References Cited

U.S. PATENT DOCUMENTS

| | | | |
|---|---|---|---|
| 4,627,837 | 12/1986 | Gonzalo | 604/101 |
| 4,705,041 | 11/1987 | Kim. | |
| 5,024,617 | 6/1991 | Karpiel | 606/47 |
| 5,035,696 | 7/1991 | Rydell | 606/47 |
| 5,062,847 | 11/1991 | Barnes | 606/194 |
| 5,075,062 | 12/1991 | Karpiel | 264/173 |
| 5,152,772 | 10/1992 | Sewell, Jr. | 606/159 |
| 5,201,732 | 4/1993 | Parins et al. | 606/47 |
| 5,241,970 | 9/1993 | Johlin, Jr. et al. | 128/772 |

FOREIGN PATENT DOCUMENTS

| | | | |
|---|---|---|---|
| 1724183 | 4/1992 | U.S.S.R. | 128/898 |
| 1826868 | 7/1993 | U.S.S.R. | 128/898 |

OTHER PUBLICATIONS

Burton, Postcholecystectomy Syndrome, Mar. 4, 1992, Post.Grad. Med. 91:255-8.

Jones et al., Sphincteroplosty for Recurrent Pancreatitis: A Second Report Ann.Surg. 147:180,1958.

Jones et al., Choledochoduodenostomy to Prevent Residual Stones, Arch.Surg. 86:1014, 1963.

Jones et al., Transduodenal Sphincteroplasty (Not Sphincterotomy) for Biliary and Pancreatic Disease, Am.J.Surg. 118:292, Aug.1969.

Moody et. al., Transduodenal Sphincteroplasty and Transampullary Septectomy for Postcholecystectomy Pain, Ann.Surg. 197:627 1983.

*Primary Examiner*—Angela D. Sykes
*Assistant Examiner*—Samuel Gilbert
*Attorney, Agent, or Firm*—Joseph K. Andonian

[57] ABSTRACT

A surgical process for the complete functional inactivation of the Sphincter of Oddi for the purpose of treating accurately diagnosed functional abnormality of the Sphincter of Oddi complex.

4 Claims, 3 Drawing Sheets

SURGICAL METHOD

This invention relates to a method for the surgical repair of the Sphincter of Oddi leading to complete functional inactivation.

BACKGROUND PRIOR ART

The Sphincter of Oddi is the muscular mechanism that controls the flow of bile and pancreatic fluid into the duodenum. Both bile and pancreatic fluid enter the duodenum through ducts that converge at the Papilla of Vater, a small nipple shaped projection just inside the duodenal mucosa. When the flow of fluid is seriously inhibited or inappropriately regulated to meet digestive requirements, surgical intervention is sometimes desirable. Moody et al., Transduodenal Sphincteroplasty and Transampullary Septectomy for Postcholecystectomy Pain, *Ann. Surg.* 197:627 May, 1983, reported on the use of surgery on the sphincter for severe incapacitating pain following removal of the gall bladder. Jones et al., Transduodenal Sphincteroplasty (Not Sphincterotomy) for Biliary and Pancreatic Disease, *Am.J.Surg.*, 118:292, August, 1969, reported on the use of surgery on the sphincter for biliary and pancreatic disease.

SUMMARY OF THE PRESENT INVENTION

The present invention differs from the referenced procedures both in the surgical procedures used and the specific indications for the surgery itself. Both prior art methods cut into the sphincter where it surrounds the common duct and excise the transampulary septum that separates the common duct from the pancreatic duct. In addition to those incisions, the present method inter alia also cuts into the sphincter where it surrounds the pancreatic duct. Although the present method (and sometimes the prior art) is limited to a patient population unequivocally exhibiting functional abnormality of the Sphincter of Oddi complex, it can be successfully used in a larger segment of that population than the prior art methods.

The patient population suitable for treatment with the method of the present invention is characterized (a) by biliopancreatic pain unexplained by other causes, (b) by negative abdominal ultrasound and upper gastrointestinal series examinations, (c) by unresponsiveness to medical therapy, and (d) by elevated basal and/or peak pressures on biliary manometry. The elevated basal and peak pressures on biliary manometry used to determine suitability of patients for use of the present method are lower than those recommended in the prior art. For example, Burton, Postcholecystectomy Syndrome, *Postgrad.Med.J.*, 91(4):256–8, March, 1992, limits its recommendation for use of sphincteroplasty to a patient population exhibiting a peak wave pressure (mm Hg) exceeding 220 and a wave frequency (per min) exceeding 10. The present method has been successfully employed in patients exhibiting a peak wave pressure as low as 160 and a wave frequency as low as 8. This success is due in no small part to the use of electrocoagulation to assure clear vision in the course of surgery whose goal is to more completely and assuredly inactivate the Sphincter of Oddi. Since the digestive system can function satisfactorily without an active Sphincter of Oddi, inactivation is preferable to a malfunctioning sphincter. When employed by properly trained and qualified surgeons in accurately diagnosed patients, the present invention has resulted in a success rate of 88% as reported in questionnaires by the patients on whom the surgery was performed.

OBJECTS OF THE INVENTION

The principal object of the present invention is to treat accurately diagnosed functional abnormality of the Sphincter of Oddi complex with more assured surgical inactivation of the Sphincter and relief of the symptoms associated therewith.

Other objects will be apparent from the following description.

Figure 1:
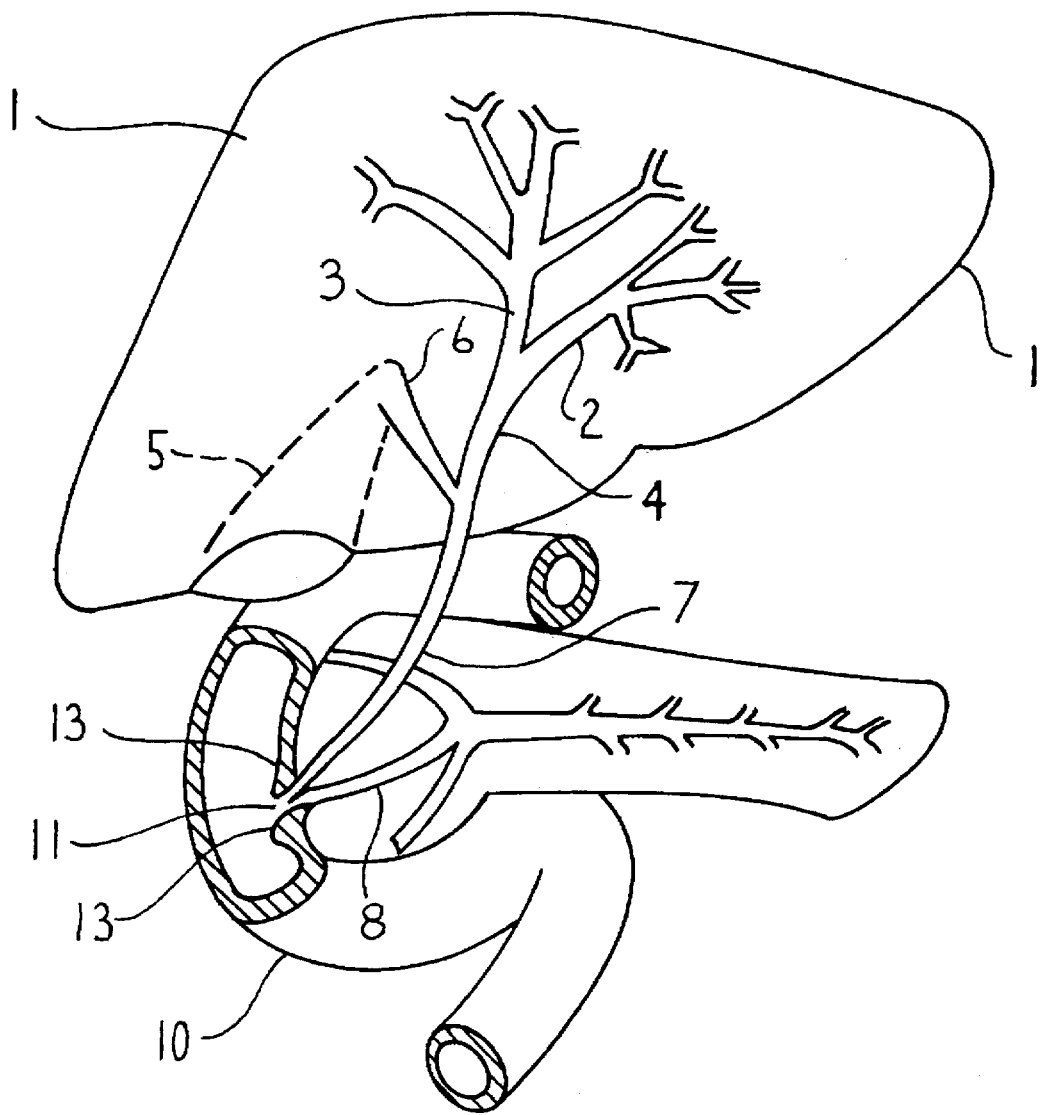
FIG. 1 is a schematic representation of the various parts of the human anatomy associated with the present surgical procedure.

Reference numerals used in the drawings:

1 Liver
2 Left hepatic duct
3 Right hepatic duct
4 Common hepatic duct
5 Gall bladder
6 Cystic duct
7 Common bile duct
8 Pancreatic duct
9 Duodenal wall
10 Duodenum
11 Major papilla
12 Septum between the common bile duct and pancreatic duct
13 Sphincter of Oddi
14 Place where mucosa of common bile duct is sutured to mucosa of duodenum.
15 Place where mucosa of common bile duct is sutured to mucosa of pancreatic duct.
16 Place where mucosa of pancreatic duct is sutured to mucosa of duodenum.

DETAILED DESCRIPTION OF THE PREFERRED EMBODIMENT

After selecting and preparing a suitable patient using previously described criteria, a right subcostal incision (i.e., an incision below the right side of the rib cage) is made and carried into the peritoneal cavity (i.e., through the membrane lining the abdominal wall). FIG. 1 depicts a portion of the human anatomy which includes the principal organs affected by the present surgical procedure. Normally the liver 1 secretes bile from the left 2 and right 3 ducts into the common hepatic duct 4 which flows into the common bile duct 7 into the duodenum 10 to meet metabolic requirements. When metabolic requirements are satisfied the Sphincter of Oddi 13 closes down and forces bile back up through the common bile duct 7 through the cystic duct 6 for storage in the gall bladder 5. Pancreatic enzymes also flow from the pancreas through the pancreatic duct 8 into the duodenum 10 through the papilla 11. However, as previously indicated the present surgical procedure is reserved for situations where the this system is not functioning normally.

A Bookwalter retractor is positioned to maintain the opening. If not already removed by prior surgery, the gall bladder 5 is surgically removed in the standard fashion. Appropriate incisions are made to detach the duodenum 10 from the abdominal wall, a maneuver known as a generous Kocher maneuver. A very thin catheter (not shown in the drawings), preferably a size 5 French pediatric feeding tube, is next used to penetrate the remnant of the gall bladder duct 6 through the duct 6 and major papilla 11, a nipple shaped projection formed where the gall bladder duct 6 joins the common liver duct 4 to form the common bile duct 7 and empties into the second portion of the duodenum 10.

Figure 2:
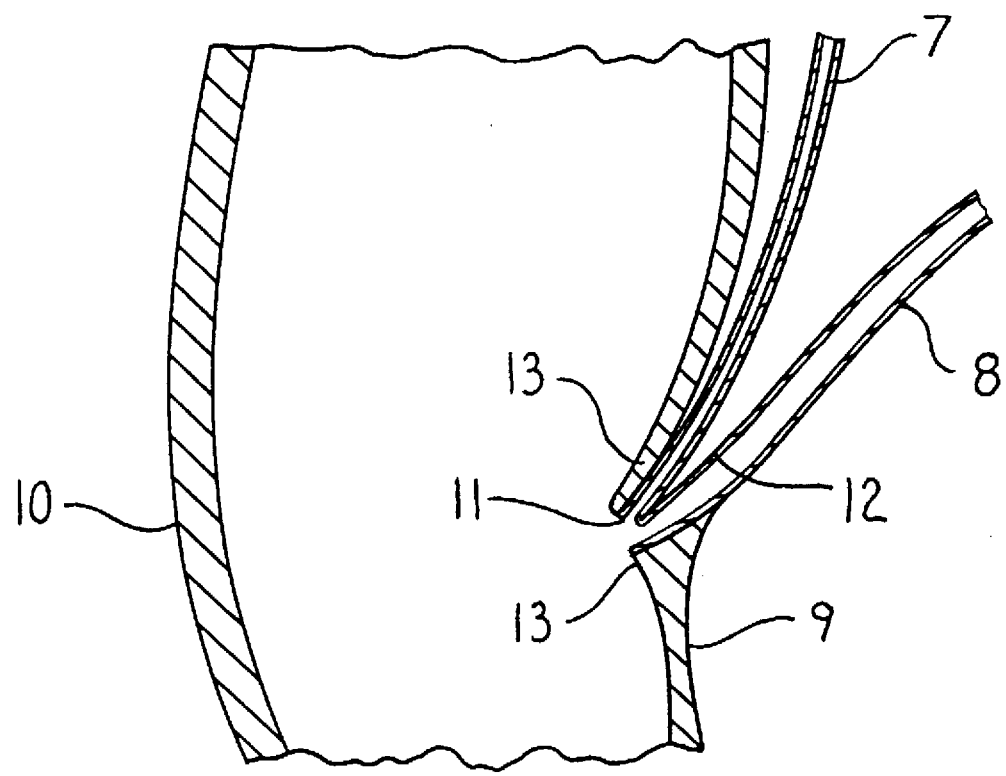
FIG. 2 a schematic representation of a segment of FIG. 1 which more clearly displays the part of the duodenum which includes the Sphincter of Oddi and the associated bile and pancreatic ducts.

A longitudinal incision is made in the duodenum 10 over the point where the catheter enters the duodenum 10. A transverse incision over the same point can also be employed to open the duodenum 10. FIG. 2 depicts an opened segment of the duodenum 10 to expose the two ducts 7 and 8 emptying into the duodenum 10 through the papilla 11. The duodenal mucosa is grasped with an intestinal Allis clamp away from the exit site of the catheter and the pancreatic ductal 8 orifice. A traction stitch of 5-0 Vicryl is then passed through the duodenal wall 9 under the clamp and the clamp is released to let the suture continue the traction on the papilla 11.

A Valley Lab electrocoagulator (a device used to coagulate blood by biterminal high frequency electric current) is then turned to a low setting, i.e., a setting of approximately 10 in spray mode. Needle tip electrocoagulation of the mucosa and submucosa of the duodenum 10 in the area directly over the common duct 7 is carried out. The use of electrocoagulation is an important feature of the present procedure and ensures inter alia a bloodless field and more complete inactivation when the bile duct 7 sphincter is incised. The bile duct 7 portion of the Sphincter of Oddi 13 (the sheath of muscle fibers that surround the associated bile and pancreatic passages collectively and individually where they approach and pass through the wall 9 of the duodenum 10) is incised over the catheter. Bleeding vessels are subjected to low-level needle tip electrocoagulation. The mucosa of the duodenum 10 is brought into contact with the mucosa on the lateral side of the common duct 7 (i.e., the side opposite the pancreatic duct 8, shown as position 14 in FIG. 3) using interrupted 5-0 Vicryl sutures. Coagulation, incision and suturing is then carried out in a step-wise fashion until the common bile duct 7 portion of the Sphincter of Oddi 13, which begins outside and passes completely through the wall 9 of the duodenum 10, is completely divided. A suture is then placed at the apex of the incision, i.e. the furthest point to which the incision is carried.

The catheter is then partially withdrawn temporarily to allow Bakes dilators to be inserted into the common duct 7 to make sure there are no obstructions. Sounding is done sequentially beginning with a size 3 up through a size 6 if possible. The dilator is never forced but must pass through the duct easily. Following sounding the catheter is then redirected through the common duct 7 and clamped to put traction directly on the common bile duct 7.

The pancreatic ductal 8 orifice is then sounded with a slender flexible probe known as a lacrimal probe, usually a size 4-0. The pancreatic portion of the Sphincter of Oddi 13 (which surrounds the pancreatic duct 8 also known as the Duct of Wirsong) is then incised sharply without prior electrocoagulation. Any resulting bleeding vessels are then subjected to brief extremely low-level electrocoagulation. The incision is then continued through the entire pancreatic portion of the Sphincter of Oddi 13, which again extends through and just outside the duodenal wall 9. The cutting portion of the surgery is completed by excising the septum 12, the dividing wall between the pancreatic and common ducts. At this point the various parts of the Sphincter of Oddi 13 (including the superior, submucosal and inferior parts of Sphincter of Boyden, the complete common duct 7 sphincter and the complete pancreatic duct 8 sphincter) are completely incised and the Sphincter of Oddi 13 is completely inactivated.

Figure 3:
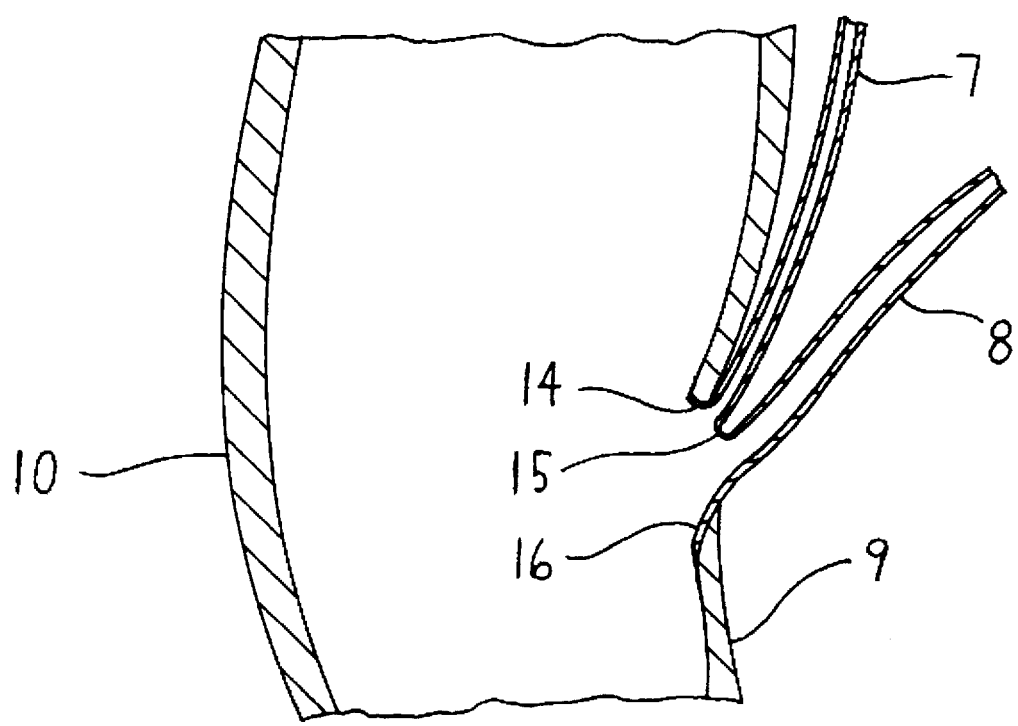
FIG. 3 the same segment as FIG. 2 after the surgery has been performed.

Interrupted 6-0 prolene sutures are then used to bring mucosa of the pancreatic duct 8 into contact with mucosa from the common duct 7 across the area left by the resected septum 12, shown as position 15 in FIG. 3. Interrupted 7-0 prolene is then used to bring mucosa of the duodenum 10 into contact with mucosa in the middle of the underside of the pancreatic duct 8, shown as position 16 in FIG. 3. A suture is then placed on the apex. The pancreatic duct 8 is then sounded with lacrimal probes sequentially up to a size 8. Again these probes are never forced but must pass easily.

The mucosa in the medial portion of the common duct 7 are sutured to mucosa of the duodenum 10 (shown as position 14 in FIG. 3) with a size 1 lacrimal probe in the pancreatic duct 8 to ensure that these sutures do not encroach upon the pancreatic duct 8. The pancreatic duct 8 is again sounded with the largest lacrimal probe that will pass easily.

The catheter in the common duct 7 is removed and the duodenum 10 is next closed in two layers using interrupted 3-0 Ethibond sutures over-running inverting 4-0 Vicryl sutures. The cystic duct 6 remnant is ligated, the right upper quadrant thoroughly irrigated and suctioned, and the position of the nasogastric tube is verified in the stomach. A size 10 flat Jackson-Pratt drain is then brought through a separate stab incision next to and made to lie adjacent to the duodenal closure. The abdomen is then closed in layers to complete the surgical procedure.

The foregoing description is a preferred embodiment of the present invention and is not intended to be inclusive of every modification and variation that can be utilized without departing from the spirit and letter of the invention as embodied in the more general language of the appended claims.

What is claimed is:

1. A surgical process performed on a human subject having an abnormality in the subject's sphincter of Oddi to inactivate the sphincter, a sheath of muscle fibers investing the subject's associated common bile and pancreatic ducts which share a septum as the ducts traverse the subject's duodenal wall to carry bile and pancreatic juice through their lumens out of a papilla or orifice emptying into the duodenum, the process comprising the steps of:

exposing the subject's duodenum and gall bladder, if the latter is still present, by making a frontal subcostal right upper quadrant incision through the subject's abdominal wall into the subject's peritoneal cavity, removing the subject's gall bladder, if present, using conventional procedures leaving a cystic duct remnant, cannulating whatever remains of the subject's cystic duct after removal of the gall bladder using a very fine catheter by passing the catheter through the common bile duct and the papilla formed where the common bile duct empties into the duodenum, mobilizing the duodenum which is attached on a part of its outer surface to the subject's abdominal wall by detaching the duodenum from the subject's abdominal wall, making an incision through the subject's duodenal wall over the papilla where the catheter enters the duodenum and opposite the part of the duodenum that attached the duodenum to the subject's abdominal wall, placing a suture distal to the papilla to place the papilla on traction, incising the entire common bile duct portion of the sphincter in a stepwise fashion, carrying the incision over the catheter to an apex distal to the papilla, into the lumen of the duct until that portion of both the sphincter and duct wall are completely divided employing low-level electrocoagulation to ensure a bloodless field, subjecting any bleeding vessels to low level electrocoagulation, suturing mucosa of the duodenum to mucosa of the common bile duct on a side of the incision lateral to the pancreatic duct in a stepwise fashion as the sphincter is transected, electrocoagulating, incising and suturing in a step-wise fashion until the entire common bile duct portion of the sphincter is completely divided, placing a suture at the apex of the completed incision, partially withdrawing the catheter and sounding the common bile duct sequentially with progressively larger sized dilators to make sure there are no obstructions which would prevent easy passage of the dilators, redirecting the catheter through the common bile duct using a clamp to put traction directly on the common bile duct, cannulating the pancreatic ductal orifice with a slender flexible probe, incising the entire pancreatic portion of the sphincter in a stepwise fashion, carrying the incision to an apex distal to the orifice, into the lumen of the pancreatic duct guided by the slender probe, until that portion of both the sphincter and the duct wall are completely divided without prior electrocoagulation, subjecting any bleeding vessels to brief extremely low-level electrocoagulation, excising the septum between the pancreatic and common bile ducts, suturing mucosa of the pancreatic duct to mucosa of the common bile duct across area left after excising the septum, suturing mucosa of the duodenum to mucosa of the pancreatic duct on the duct's inferior wall in a stepwise fashion as the sphincter is dissected, placing a suture at the apex of the incision of the portion of the sphincter investing the pancreatic duct, sounding the pancreatic duct sequentially with progressively larger sized dilators to make sure there are obstructions which would prevent easy passage of the dilators, placing a very thin probe in the pancreatic duct to ensure that subsequent suturing does not occlude the lumen of the pancreatic duct, suturing mucosa of the duodenum to mucosa of the common bile duct medially, sounding the pancreatic duct with as large a probe as will pass easily through the duct to ascertain that suture placement has not occluded the lumen of the duct, removing the catheter from the common bile duct, removing the traction suture distal to the papilla, closing and suturing the duodenum in two layers, ligating the cystic duct remnant, irrigating and suctioning the right upper quadrant of the abdomen thoroughly, bringing a flat drain through a separate stab incision in the abdominal wall adjacent to the duodenal closure, and closing the abdomen in layers.

2. The process of claim 1 wherein the surgery is performed on a human subject with an unequivocally functional abnormality of the sphincter of Oddi complex.

3. In a surgical process to inactivate a sphincter of Oddi of a human subject having an abnormality in said sphincter, a sheath of muscle fibers investing associated common bile and pancreatic ducts of said subject as said ducts traverse said subject's duodenal wall, the improvement comprising incising the common bile component of the subject's sphincter using electrocoagulation and suturing in a step-wise fashion to ensure that the common bile duct component of the subject's sphincter is completely and accurately divided and subsequently incising the entire pancreatic duct component of the subject's sphincter without prior electrocoagulation.

4. The process of claim 3 wherein the surgery is performed on a human subject having an unequivocally functional abnormality of the subject's sphincter of Oddi complex.

\* \* \* \* \*